(12) United States Patent
Hansen et al.

(10) Patent No.: US 7,223,260 B2
(45) Date of Patent: May 29, 2007

(54) COLLECTING BAG HAVING AN IMPROVED CLOSURE

(75) Inventors: Soren Hansen, Helsinger (DK); Lars Bo Poulsen, Helsinger (DK)

(73) Assignee: Coloplast A/S, Humlebaek (DK)

( * ) Notice: Subject to any disclaimer, the term of this patent is extended or adjusted under 35 U.S.C. 154(b) by 112 days.

(21) Appl. No.: 10/674,428

(22) Filed: Oct. 1, 2003

(65) Prior Publication Data
US 2004/0068243 A1    Apr. 8, 2004

(30) Foreign Application Priority Data
Oct. 2, 2002   (DK) .......................... PA 2002 01474

(51) Int. Cl.
*A61M 1/00*   (2006.01)
(52) U.S. Cl. .................. 604/327; 604/317; 604/332; 604/337; 604/338; 604/339; 604/345; 383/31; 383/98
(58) Field of Classification Search ............... 604/327, 604/317, 318–326, 328–355; 383/87–89, 383/31, 98; 4/144.1; 292/125
See application file for complete search history.

(56) References Cited

U.S. PATENT DOCUMENTS

| | | | | |
|---|---|---|---|---|
| 3,690,320 A | | 9/1972 | Riely | ........................ 128/283 |
| 3,825,005 A | | 7/1974 | Fenton | ....................... 128/283 |
| 4,755,177 A | * | 7/1988 | Hill | ............................. 604/336 |
| 6,589,221 B1 | * | 7/2003 | Olsen et al. | ................. 604/332 |
| 6,726,667 B2 | * | 4/2004 | Leise et al. | .................. 604/339 |
| 6,780,172 B2 | * | 8/2004 | Olsen et al. | ................. 604/332 |
| 2004/0049837 A1 | * | 3/2004 | Falconer et al. | ............. 4/144.1 |

FOREIGN PATENT DOCUMENTS

| | | |
|---|---|---|
| EP | 0 013 109 | 7/1980 |
| EP | 001197193 A2 * | 4/2002 |
| GB | 2 000 683 | 1/1979 |
| GB | 2 268 065 | 1/1994 |
| WO | 96/19164 | 6/1996 |
| WO | 99/25278 | 5/1999 |
| WO | 99/66859 | 12/1999 |
| WO | 01/28470 | 4/2001 |
| WO | 02/13737 | 2/2002 |
| WO | WO 03/065944 A1 * | 8/2003 |

* cited by examiner

*Primary Examiner*—Tatyana Zalukaeva
*Assistant Examiner*—Ginger T. Chapman
(74) *Attorney, Agent, or Firm*—Jacobson Holman PLLC

(57) ABSTRACT

The collecting bag has a bag member formed by a first and a second film blank, and a discharge portion that is foldable and unfoldable to bring the discharge portion from an open unfolded condition to a closed folded condition and vice versa. A first plate member is positioned on the first film blank and a second plate member is positioned on an extension of the second film blank. Each plate member is formed from a relatively stiff material, and the distance between the distal edge of the first plate member and the proximal edge of the second plate member is smaller than the thickness of the first plate member. When folding the discharge portion, the distal edge of the first plate member acts as a pivot, and a stretching effect is created on the second film blank to effectively seal the discharge opening without deformation of the plate members.

20 Claims, 1 Drawing Sheet

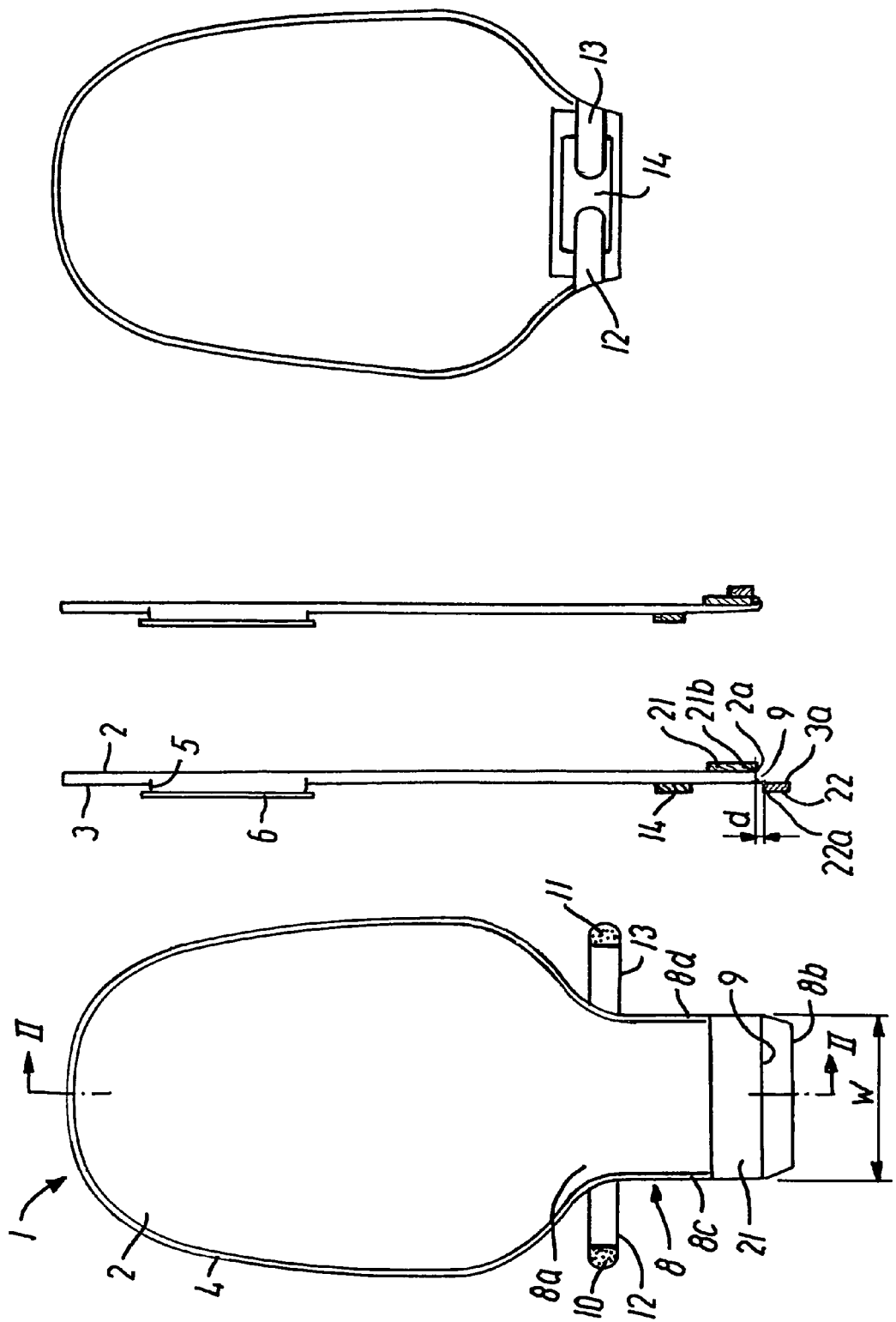

COLLECTING BAG HAVING AN IMPROVED CLOSURE

CROSS-REFERENCE TO RELATED APPLICATIONS

The present application claims the benefit of priority from Danish Patent Application No. PA 2002 01474 filed on Oct. 2, 2002.

BACKGROUND OF THE INVENTION

The invention relates to a collecting bag for human body wastes, comprising a bag member and a discharge portion defining a longitudinal direction. The discharge portion is foldable and unfoldable by at least one folding in said longitudinal direction between to bring the discharge portion from an open unfolded condition to a closed folded condition and vice versa, and a locking device is provided at the discharge portion for locking the bag in said closed folded condition of the discharge portion.

This type of drainable collecting bags are often used as ostomy bags. In the case of ileostomy patients and colostomy patients with uncontrolled release of faeces of a more or less fluid consistence, the collecting bag has to be emptied rather frequently, and the closure device thus has to be easy to open and re-close after emptying and at the same time provide a reliable and tight seal in operation, i.e. between emptyings.

Several different designs of closure devices have been developed and are generally known.

For instance, U.S. Pat. No. 3,690,320 and GB patent applications Nos. 2 268 065 and 2 000 683 disclose collecting bag with closure devices, in which strips of the interlocking-elements type, such as VELCEO hook and loop fastening elements, are placed on each of the film blanks of the discharge portion and which after folding the discharge portion tightly are brought into contact with each other.

A further design is shown in EP patent application No. 0 013 109, in which the outlet portion is folded and subsequently tucked into a gap formed by a semirigid strip attached to the bag wall.

In a still further design of a resealable closure device for an ostomy bag, disclosed in U.S. Pat. No. 3,825,005 and similar to so-called mini-grip closures frequently used in plastic foil bags for packaging purposes, a sealed closure is provided by engagement between parallel ribs or linear protuberances formed by panels attached to either of the two film blanks.

It is a disadvantage in all of the above designs that accurate and correct handling of the closure device is required in order to provide the necessary seal against leakage in the closed position of the bag. In particular, the tight folding of the discharge portion and the tucking operation of the discharge portion and the mini-grip-like closure disclosed in the two latter documents may cause problems, especially to users having e.g. reduced dexterity.

Another type of closure device is shown in published international application No. WO 96/19164, in which the discharge portion is rolled up on a locking clip fastened to one of the film blanks. The clip comprises a resilient zone which for instance may be provided as an outer layer of integral foam plastic surrounding a semi-rigid core body. Although the collecting bag and locking clip of this document provide for an improved tightness in comparison with the devices described in the above, the choice of design of the locking device is limited, as the sealing effect is dependent on the locking clip.

International application No. WO 99/66859 discloses a collecting bag of the kind mentioned in the introduction that alleviates a number of the disadvantages outlined in the above by the use of one or more resilient seal members positioned at or near the discharge opening. The resilience of the member or members provides an efficient sealing effect at the beginning and the end, respectively, of the folding operation.

Although closure of this collecting bag is carried out to satisfaction in a number of applications, it has turned out that particularly in collecting bags having a relatively wide discharge portion, the seal member or members may be deformed to such an extent during the initial folding operation that it becomes difficult to obtain a sufficient contact between the relevant portions of the surfaces of the seal member and the film blank, or the seal members.

BRIEF SUMMARY OF THE INVENTION

With this background it is an object of the present invention to improve a collecting bag of the kind mentioned in the introduction with respect to reliability and ease of operation.

This and further objects are met by the provision of a collecting bag for human body wastes, comprising a bag member formed by a first and a second film blank with joined edges, an inlet opening being provided in one of said first and second film blanks, a discharge portion defining a longitudinal direction and starting at a proximal end at a distance from the inlet opening and extending between two end sections of said film blanks to a distal end, wherein said second film blank is provided with an extension extending beyond a distal edge of said first film blank, a discharge opening being formed between said extension and the distal edge of the first film blank, said discharge portion being foldable and unfoldable by at least one folding in said longitudinal direction between the distal and proximal ends to bring the discharge portion from an open unfolded condition to a closed folded condition and vice versa, and wherein a locking device is provided at the discharge portion for locking the bag in said closed folded condition of the discharge portion, in which the collecting bag includes a first plate member positioned on the first film blank and a second plate member positioned on the extension of the second film blank, each plate member having a predetermined height in the longitudinal direction of the discharge portion between a proximal edge and a distal edge, a predetermined width in a direction transverse to the longitudinal direction, and a predetermined thickness, each plate member being formed from a relatively stiff material, and the distance between the distal edge of the first plate member and the proximal edge of the second plate member being smaller than the thickness of the first plate member.

By the combination of forming the plate members from a relatively stiff material and the positions of the plate members with respect to each other, i.e. with a small distance between the plate members in the longitudinal direction of the discharge portion, the folding operation is facilitated even in case of wide discharge portions. Surprisingly, it turns out that sufficient tightness is achieved, even though virtually no deformation of the plate members in the thickness direction takes place. During the folding of the discharge portion the distal edge of the first plate member provides a pivot which, due to the thickness of the first plate member in combination with the small distance between this distal edge and the proximal edge of the second plate member, gives rise to a tensional force in the longitudinal direction of at least the second film blank and consequently, the elasticity of the film blanks provides a sealing force.

Preferably, the first plate member has a larger height than the second plate member. This makes it possible to form the collecting bag with a short and compact design of the discharge portion. The ratio between the heights of the first and the second plate member may e.g. lie in the interval from 1:1 to 4:1 depending on the height of the first plate member.

With the present invention, it is possible to utilize discharge portions having a substantial width. The dimensions of the first plate member may vary, and in an advantageous embodiment, the first plate member has a height-width ratio in the interval from 1:7 to 1:2.

In order to facilitate emptying and cleaning of the bag, the first and/or the second plate member may have an arc-shaped configuration with respect to the plane of the discharge portion. This will incur a tendency to open the discharge opening slightly in the unfolded condition and ease further opening when pressing slightly on the side edges of the discharge portion in the area of the plate members.

In a preferred embodiment, the second plate member is positioned on the outer side of the extension of the second film blank. The surface beyond the distal edge of the first plate member and the distal edge of the discharge portion is thus smooth and very easy to clean.

Preferably, the locking device is provided close to the proximal end of said discharge portion to allow folding of said discharge portion by at least one subsequent folding following said at least one folding. The at least one subsequent folding may be defined by the proximal edge of the first plate member. The locking device may comprise foldable locking strips projecting from opposite side edges of the discharge portion and being provided at one surface with first locking means engageable with second locking means provided on a surface part of said discharge portion, said second locking means being located in alignment with said locking strips after said at least one subsequent folding.

Further features and advantages may readily be appreciated from the following detailed description.

BRIEF DESCRIPTION OF THE SEVERAL VIEWS OF THE DRAWINGS

In the following the invention will be described in further detail with reference to preferred embodiments and the several views of the schematic drawings, in which FIG. 1 shows a plane view of an embodiment of a collecting bag according to the invention, seen from the side intended to face away from the user and in the fully open position;

FIG. 2 shows a longitudinal section of the collecting bag along the line II—II in FIG. 1;

FIG. 3 is a schematic view corresponding to FIG. 2 of the collecting bag in a first folded position; and FIG. 4 is a view corresponding to FIG. 1 in the fully closed position of the bag.

DETAILED DESCRIPTION OF THE INVENTION

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In FIGS. 2 and 3 some sectional areas are indicated by fully drawn lines in order not to impede the clear reading of the drawings.

The collecting bag shown in the drawings is designed as an ostomy bag of a generally known and common type and comprises a bag member 1 formed by first and second film blanks 2,3 which are joined along their edges by means of a seam 4 made by welding or in any other convenient manner. The film blanks may be made from a suitable flexible plastic sheet or foil material that possesses at least some degree of elasticity as will be described further on.

Each film blank 2,3 has an inner side that is intended to face the contents of the bag and an outward facing outer side.

In the second film blank 3, the outer side of which is intended to face the user in a position of use, and thus forms the back wall of the bag, an inlet opening 5 is provided which in a manner known per se is surrounded by connecting elements 6 for connection of the bag to a body orifice, i.e. in this case an intestinal orifice in the form of a so-called stoma in the user's abdominal wall.

At a distance from the inlet opening 5, the bag is designed with a discharge portion 8 starting at a proximal or neck end 8a and extending to a distal or terminal end 8b. The discharge portion 8 is formed by two end sections of the film blanks 2,3 and is likewise joined along opposed side edges 8c and 8d.

In the vicinity of the distal end 8b of the discharge portion 8, a discharge opening 9, through which the bag may be emptied of its contents, is formed by a slit between the two film blanks 2,3. The discharge opening 9 is formed between an extension 3a of the second film blank 3 and a distal end edge 2a of film blank 2.

The bag is brought from the open or discharge position shown in FIGS. 1 and 2 to a position of use, in which the bag is closed, by a number of folding operations and in a manner that will be described in further detail below. In order to keep the collecting bag in the closed position, a locking device is provided, which in the embodiment shown comprises foldable locking strips 12 and 13 projecting from the side edges 8c and 8d of the discharge portion 8 at the proximal end 8a thereof. The projecting foldable locking strips 12 and 13, which may be formed integrally with one of or both the film blanks 2,3, are provided with a first set of locking means, which in the embodiment shown is constituted by male VELCRO hook and loop fastening elements 10,11, but which may also comprise snap fastening members, different types of adhesive members etc. and are releasably engageable with a second set of mating locking means provided on the back side of the second film blank 3. In the embodiments shown, the second set of locking means is constituted by a plate 14 of female VELCRO hook and loop fastening elements. It should be noted that the locking device may be designed in other ways, e.g. as described in applicant's International application No. WO 99/25278, or as a traditional locking clip.

A first plate member 21 is provided at the distal edge 2a of the first film blank 2. A second plate member 22 is provided on the extension 3a of the second film blank 3. The plate members 21,22 are made from a suitable, relatively stiff semi-rigid material, e.g. nylon, high-density polyethylene, polypropylene, styrene etc. The plate members may e.g. be formed from the same material as the film blanks themselves, although in a considerably larger thickness. The plate members may be made from identical materials and have the same thickness, or possess different properties. For instance, the plate members may be cut as solid plates from an appropriate sheet material.

In the embodiment shown, the first plate member 21 is positioned on the front side of the discharge portion, i.e. on the outer side of the first film blank 2, and the second plate member 22 is positioned on the back side of the discharge portion, i.e. on the outer side of the extension 3a. In the embodiment shown, the first plate member 21 has a generally rectangular shape, whereas the second plate member 22 has a generally trapezoid shape, the second plate member 22 having at the proximal edge 22a a corresponding width w as the distal edge 21b of the first plate member 21. In the embodiment shown, the first and second plate members 21,22 are positioned in such a way that a small spacing or clearance occurs between the edges facing each other, i.e. the proximal edge 22a of the second plate member 22 and the distal edge 21b of the first plate member 21. Generally, the distance d between the facing edges 21b,22a should be smaller than the thickness of the first plate member 21. It is possible to position the first and second plate members 21, 22 such that the distance between the facing edges is substantially eliminated, i.e. that the edges are positioned opposite each other, or even that the edges overlap each other slightly. However, such an overlapping relationship presupposes that the proximal edge of the second plate member 22 is e.g. softer or rounded, that the degree of elasticity of at least the second film blank is higher than is the case when there is a clearance, or that the attachment between the second plate member and the film blank possesses some elasticity. The thickness of the plate members and the distance between the facing edges are optimised with respect to the elasticity, tensional strength and stretchability of the film blanks on which the plate members are arranged. In the embodiment shown, the first plate member 21 has a larger height than the second plate member 22. The ratio between the heights of the first and the second plate member may e.g. lie in the interval from 1:1 to 4:1 depending on the height of the first plate member. The second plate member 22 should, however, have such a height that it is sufficient torsional strength and stability in order to allow the folding operations to be carried out properly. The width of each of the plate members 21,22 should be larger than the distance between the joints at each side edge 8c,8d and may e.g. be such that the plate members extend over the entire width of the discharge portion. The dimensions of the first plate member may vary, e.g. within an interval of the height-width ratio ranging from 1:7 to 1:2. In the embodiment shown the height is approximately 20 mm, whereas the width is approximately 75 mm, thus resulting in a ratio of 0.27. The thickness suitably lies in the interval 0.5 to 2 mm, but values outside this interval are conceivable.

Although not clearly visible from the drawings, the first and the second plate member 21 and 22 each has an arc-shaped configuration with respect to the plane of the discharge portion 8. By forming at least one of the plate members with an arc-shaped configuration, the discharge opening will be opened slightly in the unfolded condition and ease further opening when pressing slightly on the side edges 8c,8d of the discharge portion in the area of the plate members.

When closing the bag, the discharge portion 8 is folded starting from the distal end by initially folding the second plate member 22 against the first plate member 21, using the distal edge 21b of the first plate member 21 as a pivot. As is suggested in FIG. 3, this initial folding will have a slight stretching effect on the material of the second film blank 3, whereas substantially no deformation of the plate members 21,22 in the thickness direction takes place. An effectively sealed closure of the discharge opening 9 is thus provided.

Subsequently, following this initial folding the discharge portion 8 is folded in the embodiment shown two more times until the locking means 14 are brought into alignment with the projecting locking strips 12 and 13 which are then folded to bring the locking means. 10 and 11 into engagement with locking means 14.

The invention should not be regarded as being limited to the embodiments described in the above but various modifications and combinations of the shown embodiments may be carried out without departing from the scope of the following claims.

For example, although the invention has been described only with reference to a collecting bag having two plate members, both of which are positioned on the outer side of the respective film blank, other configurations are conceivable as well, including those having more than two plate members and those in which it is the front film blank that is provided with an extension.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A collecting bag for human body wastes, comprising:
   a bag member formed by a first and a second film blank with joined edges, an inlet opening being provided in one of said first and second film blanks;
   a discharge portion defining a longitudinal direction and starting at a proximal end at a distance from the inlet opening and extending between two end sections of said film blanks to a distal end, a length of said second film blank being greater than a length of said first film blank to form an extension extending beyond a distal edge of said first film blank;
   a discharge opening being formed between said extension and said distal edge of the first film blank;
   said discharge portion being foldable and unfoldable by at least one folding in said longitudinal direction between the distal and proximal ends to bring the discharge portion from an open unfolded condition to a closed folded condition and vice versa;
   a locking device provided at the discharge portion for locking the bag in said closed folded condition of the discharge portion; and
   a first plate member positioned on the first film blank adjacent said distal edge and a second plate member positioned on the extension of the second film blank adjacent said discharge opening, each plate member having a height defined in the longitudinal direction of the discharge portion between respective proximal and distal edges of said plate member, a width defined in a direction transverse to the longitudinal direction, and a thickness, each plate member being formed from a relatively stiff material lacking in suppleness in a thickness direction, and a distance between the distal edge of the first plate member and the proximal edge of the second plate member being smaller than the thickness of the first plate member.

2. The collecting bag as claimed in claim 1, wherein the first plate member has a larger height than the second plate member.

3. The collecting bag as claimed in claim 2, wherein the first plate member has a height-width ratio in the interval from 1:7 to 1:2.

4. The collecting bag as claimed in claim 3, wherein the ratio between the heights of the first and the second plate member lies in the interval from 1:1 to 4:1.

5. The collecting bag as claimed in claim 1, wherein the first and/or the second plate member has an arc-shaped configuration with respect to the plane of the discharge portion.

6. The collecting bag as claimed in claim 1, wherein the second plate member is positioned on the outer side of the extension of the second film blank.

7. The collecting bag as claimed in claim 1, wherein said locking device is provided close to the proximal end of said discharge portion to allow folding of said discharge portion by at least one subsequent folding following said at least one folding.

8. The collecting bag as claimed in claim 1, wherein the first plate member has a larger height than the second plate member, said locking device being provided close to the proximal end of said discharge portion to allow folding of said discharge portion by at least one subsequent folding following said at least one folding, said at least one subsequent folding being defined by the proximal edge of the first plate member.

9. The collecting bag as claimed in claim 7, wherein said locking device includes foldable locking strips projecting from opposite side edges of the discharge portion and is provided at one surface with first locking elements engageable with second locking elements provided on a surface part of said discharge portion, said second locking elements being located in alignment with said locking strips after said at least one subsequent folding.

10. A collecting bag for human body wastes, comprising:
a bag member formed by a first film blank and a second film blank with joined edges, an inlet opening being provided in one of said first and second film blanks;
a discharge portion defining a longitudinal direction and extending between two end sections of said film blanks to a distal end, a length of said second film blank being greater than a length of said first film blank to form an extension extending beyond a distal edge of said first film blank;
a discharge opening formed between said extension and said distal edge of the first film blank;
said discharge portion being foldable and unfoldable by at least one folding in said longitudinal direction to bring the discharge portion from an open unfolded condition to a closed folded condition and vice versa;
a first plate member made of a relatively stiff material lacking in suppleness in a thickness direction and positioned on the first film blank and having a distal edge adjacent said first film blank distal edge;
a second plate member made of a relatively stiff material lacking in suppleness in a thickness direction and positioned on the extension of the second film blank and having a proximal edge adjacent said discharge opening; and
said first plate member distal edge and said second plate member proximal edge being separated by a distance that is smaller than a thickness of said first plate member such that, when the discharge portion is initially folded to bring the second plate member against the first plate member, the distal edge of the first plate member acts as a pivot, and a stretching effect is created on the second film blank to effectively seal the discharge opening with substantially no deformation of the plate members in the thickness direction.

11. The collecting bag as claimed in claim 10, wherein each relatively stiff plate member is formed from a material including nylon, polyethylene or polypropylene.

12. The collecting bag as claimed in claim 10 wherein each plate member has a height defined in the longitudinal direction of the discharge portion, and a width defined in a direction transverse to the longitudinal direction, the height of the first plate member being larger than the height of the second plate member.

13. The collecting bag as claimed in claim 12, wherein the first plate member has a height to width ratio of from 1:7 to 1:2.

14. The collecting bag as claimed in claim 13, wherein the ratio between the heights of the first and second plate members ranges from 1:1 to 4:1.

15. The collecting bag as claimed in claim 10, wherein the first and/or the second plate member has an arc-shaped configuration with respect to the plane of the discharge portion.

16. The collecting bag as claimed in claim 10, wherein the second plate member is positioned on the outer side of the extension of the second film blank.

17. The collecting bag as claimed in claim 10, wherein the first plate member is wholly on one side of said discharge opening and said second plate member is wholly on an opposite side of said discharge opening, the two plate members being arranged side by side longitudinally.

18. The collecting bag as claimed in claim 10, further comprising a locking device provided at a proximal end of said discharge portion for locking the bag in said closed folded condition of the discharge portion.

19. The collecting bag as claimed in claim 5, wherein said discharge opening is opened slightly in the unfolded condition as a result of said arc-shaped configuration.

20. The collecting bag as claimed in claim 15, wherein said discharge opening is opened slightly in the unfolded condition as a result of said arc-shaped configuration.

* * * * *